United States Patent
Hierold et al.

(10) Patent No.: US 10,633,335 B2
(45) Date of Patent: Apr. 28, 2020

(54) STORAGE OF 3-METHYLTHIOPROPIONALDEHYDE AND METHYL MERCAPTAN

(71) Applicant: Evonik Operations GmbH, Essen (DE)

(72) Inventors: Judith Hierold, Hannover (DE); Sascha Ceylan, Hanau (DE); Stephan Rautenberg, Bornheim (DE); Harald Jakob, Hasselroth (DE); Christian Kaiser, Waldaschaff (DE); Andrea Kopp, Kleinwallstadt (DE); Lucas Geist, Freigericht (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 15/851,362

(22) Filed: Dec. 21, 2017

(65) Prior Publication Data

US 2018/0179155 A1 Jun. 28, 2018

(30) Foreign Application Priority Data

Dec. 22, 2016 (EP) .................................. 16206225

(51) Int. Cl.

| | | |
|---|---|---|
| *C07C 323/12* | (2006.01) | |
| *C07C 323/22* | (2006.01) | |
| *C07C 321/04* | (2006.01) | |
| *C07C 319/12* | (2006.01) | |
| *C07C 47/22* | (2006.01) | |
| *C07C 319/26* | (2006.01) | |

(52) U.S. Cl.
CPC ............ *C07C 323/12* (2013.01); *C07C 47/22* (2013.01); *C07C 319/12* (2013.01); *C07C 319/26* (2013.01); *C07C 321/04* (2013.01); *C07C 323/22* (2013.01)

(58) Field of Classification Search
CPC ... C07C 319/26; C07C 323/12; C07C 323/22; C07C 321/04; C07C 319/12
See application file for complete search history.

(56) References Cited

U.S. PATENT DOCUMENTS 4,546,205 A   10/1985  Sandler

FOREIGN PATENT DOCUMENTS

| EP | 0 096 153 A2 | 12/1983 | | |
|---|---|---|---|---|
| EP | 0 096 153 A3 | 12/1983 | | |
| EP | 2 813 489 A1 | 12/2014 | | |
| FR | 1520328 A  * | 4/1968 | .............. | B01J 8/025 |
| WO | WO 93/13059 A1 | 7/1993 | | |
| WO | WO-2017140665 A1 * | 8/2017 | ........... | C07C 323/22 |

OTHER PUBLICATIONS

Extended European Search Report dated Mar. 20, 2018 in Patent Application No. 17207366.0.
U.S. Appl. No. 11/016,130, filed Apr. 3, 2007, now U.S. Pat. No. 7,199,270, Alexander Moller.
U.S. Appl. No. 08/885,044, filed Mar. 23, 1999, now U.S. Pat. No. 5,886,230, Willi Hofen, et al.
U.S. Appl. No. 08/885,043, filed Feb. 2, 1999, now U.S. Pat. No. 5,866,721, Willi Hofen, et al.
U.S. Appl. No. 13/597,852, filed May 12, 2015, now U.S. Pat. No. 9,029,597, Martin Steffan, et al.
Search Report dated Apr. 5, 2017 in European Patent Application No. EP 16 20 6225 (with English translation of category of cited documents).

* cited by examiner

*Primary Examiner* — Rosalynd A Keys
(74) *Attorney, Agent, or Firm* — Oblon, McClelland, Maier & Neustadt, L.L.P.

(57) ABSTRACT

A compound, which is 1-(1,3-bis(methylthio)propoxy)-3-(methylthio)propan-1-ol, a composition containing the compound, a method for the preparation thereof, a method for preparing 3-methylthiopropionaldehyde by reacting 1-(1,3-bis(methylthio)propoxy)-3-(methylthio)propan-1-ol with acrolein, and also to the use of 1-(1,3-bis(methylthio)propoxy)-3-(methylthio)propan-1-ol or compositions containing the compound for the storage and/or transport of 3-methylthiopropionaldehyde and/or methyl mercaptan.

12 Claims, 3 Drawing Sheets

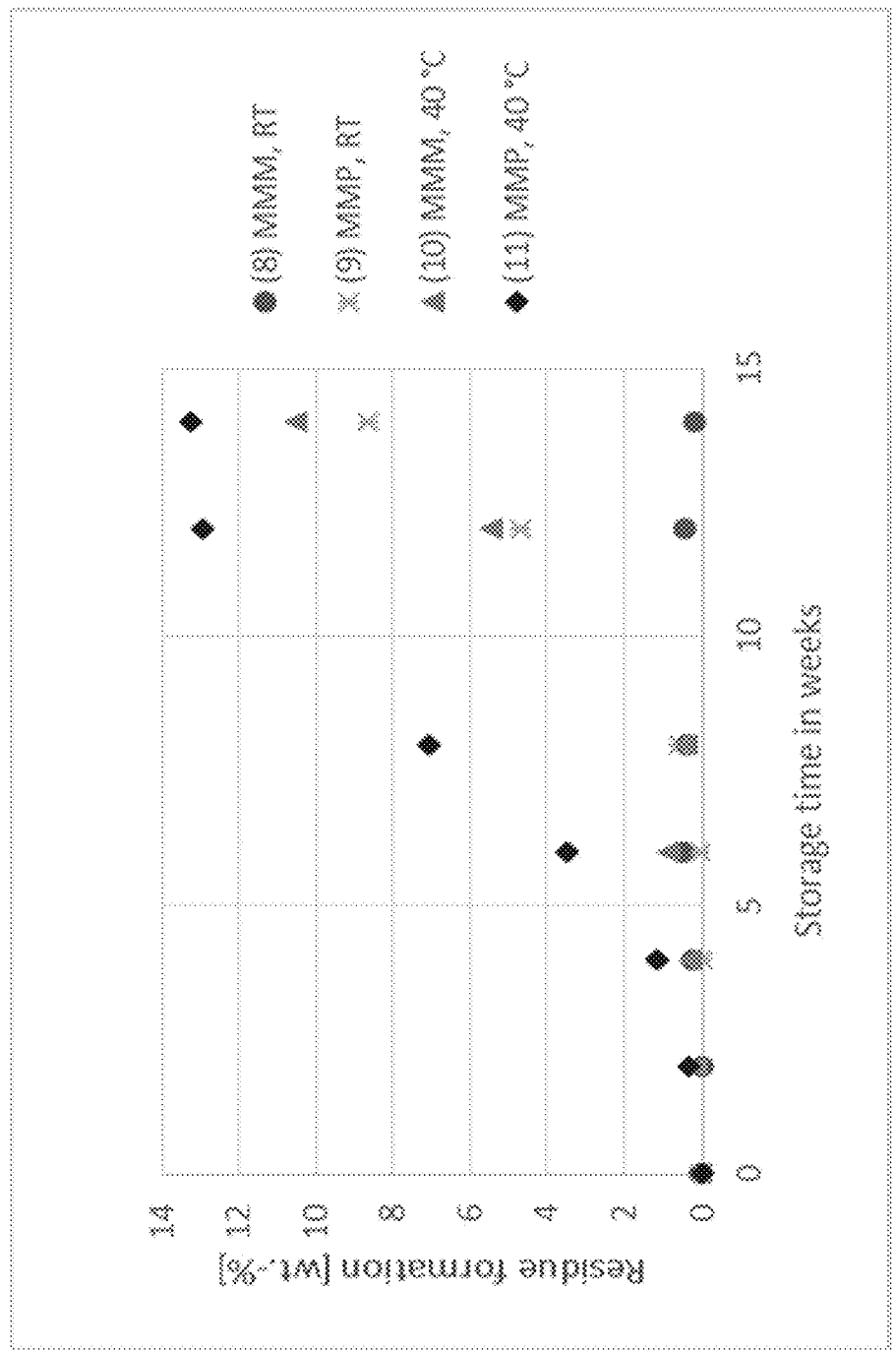
FIG. 3: Correlation of residue formation and time for examples 8 to 11 (RT = room temperature; MMM = 1-(1,3-bis(methylthio)propoxy)-3-(methylthio)propan-1-ol; MMP = 3-methylthiopropionaldehyde).

STORAGE OF 3-METHYLTHIOPROPIONALDEHYDE AND METHYL MERCAPTAN

CROSS REFERENCE TO RELATED APPLICATIONS

This application claims foreign priority to EP 16206225.1, filed Dec. 22, 2016, the entire contents of which are incorporated herein by reference.

The present invention relates to a compound according to the formula (I) with the name 1-(1,3-bis(methylthio)propoxy)-3-(methylthio)propan-1-ol, a composition comprising said compound and a method for preparing the compound according to the general formula (I) from 3-methylthiopropionaldehyde and methyl mercaptan. Furthermore, the present invention also relates to a method for preparing 3-methylthiopropionaldehyde from a compound of the general formula (I) and the use of a compound of the general formula (I) for storage and/or transport of 3-methylthiopropionaldehyde and/or methyl mercaptan.

3-Methylthiopropionaldehyde, also known by the abbreviation MMP for methylmercaptopropionaldehyde or by the name 4-thiapentanal (UN number 2785), is an important intermediate in the production of D,L-methionine and its hydroxy analogue 2-hydroxy-4-methylthiobutyric acid, also known by the abbreviation MHA for methionine hydroxy analogue. 3-Methylthiopropionaldehyde is typically prepared by reacting methyl mercaptan with acrolein by a Michael addition. The patents GB 1618884 A, GB 1173174 A and GB 1166961 A disclose methods for directly preparing 3-methylthiopropionaldehyde by reacting methyl mercaptan with acrolein or by indirectly preparing 3-methylthiopropionaldehyde, in which 3-methylthiopropionaldehyde is firstly reacted with methyl mercaptan and the reaction product thus obtained is reacted directly with acrolein to give 3-methylthiopropionaldehyde. However, these documents do not take into account the fact that the resulting 3-methylthiopropionaldehyde, as an aliphatic alpha-acidic aldehyde is not stable on storage and readily undergoes side reactions which lead to the formation of high boilers. Moreover, the compounds methyl mercaptan and acrolein used for preparing 3-methylthiopropionaldehyde are linked to a high potential risk. Both when using streams comprising acrolein or methyl mercaptan in industrial scale processes and during their storage, appropriate safety regulations must therefore be met. Due to the high vapour pressure of methyl mercaptan, a pressure vessel is also required for its storage. This makes the construction of new chemical plants and the expansion of industrial scale plants in which acrolein and methyl mercaptan are used more difficult.

A need therefore existed both for a solution to convert the compounds acrolein and methyl mercaptan into compounds with a lower risk potential and for a solution to allow the compounds 3-methylthiopropionaldehyde and methyl mercaptan to be stored in a stable and safe manner.

These objects are achieved in accordance with the invention by providing a compound of the formula (I)

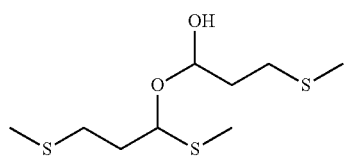

with the name according to IUPAC of 1-(1,3-bis(methylthio)propoxy)-3-(methylthio)propan-1-ol.

This compound is formed from two molecules of 3-methylthiopropionaldehyde and one molecule of methyl mercaptan. By forming this compound, the aldehyde group in 3-methylthiopropionaldehyde susceptible to oligomerization or polymerization reactions is converted into less reactive thioacetal or hemiacetal groups. The formation of high-boiling by-products by oligomerization of 3-methylthiopropionaldehyde is thereby significantly reduced. In the formation of a compound of the general formula (I), a molecule of methyl mercaptan is also incorporated. By incorporating the volatile compound methyl mercaptan into the less readily volatile compound of the general formula (I), the risk potential linked to methyl mercaptan is reduced. The compound of the general formula (I) is therefore suitable both for storage of 3-methylthiopropionaldehyde and for storage of methyl mercaptan. The compound of the general formula (I) further enables the high risk potential linked to acrolein to be reduced. Therefore, by reacting one molecule of acrolein with one molecule of the compound of the general formula (I), three molecules of 3-methylthiopropionaldehyde are formed which in turn has a distinctly lower risk potential than acrolein.

BRIEF DESCRIPTION OF THE DRAWINGS

FIG. 3 Correlation of residue formation and time for examples 8 to 11 (second test series) (RT=room temperature; MMM=1-(1,3-bis(methylthio)propoxy)-3-(methylthio)propan-1-ol; MMP=3-methylthiopropionaldehyde).

Figure 1:
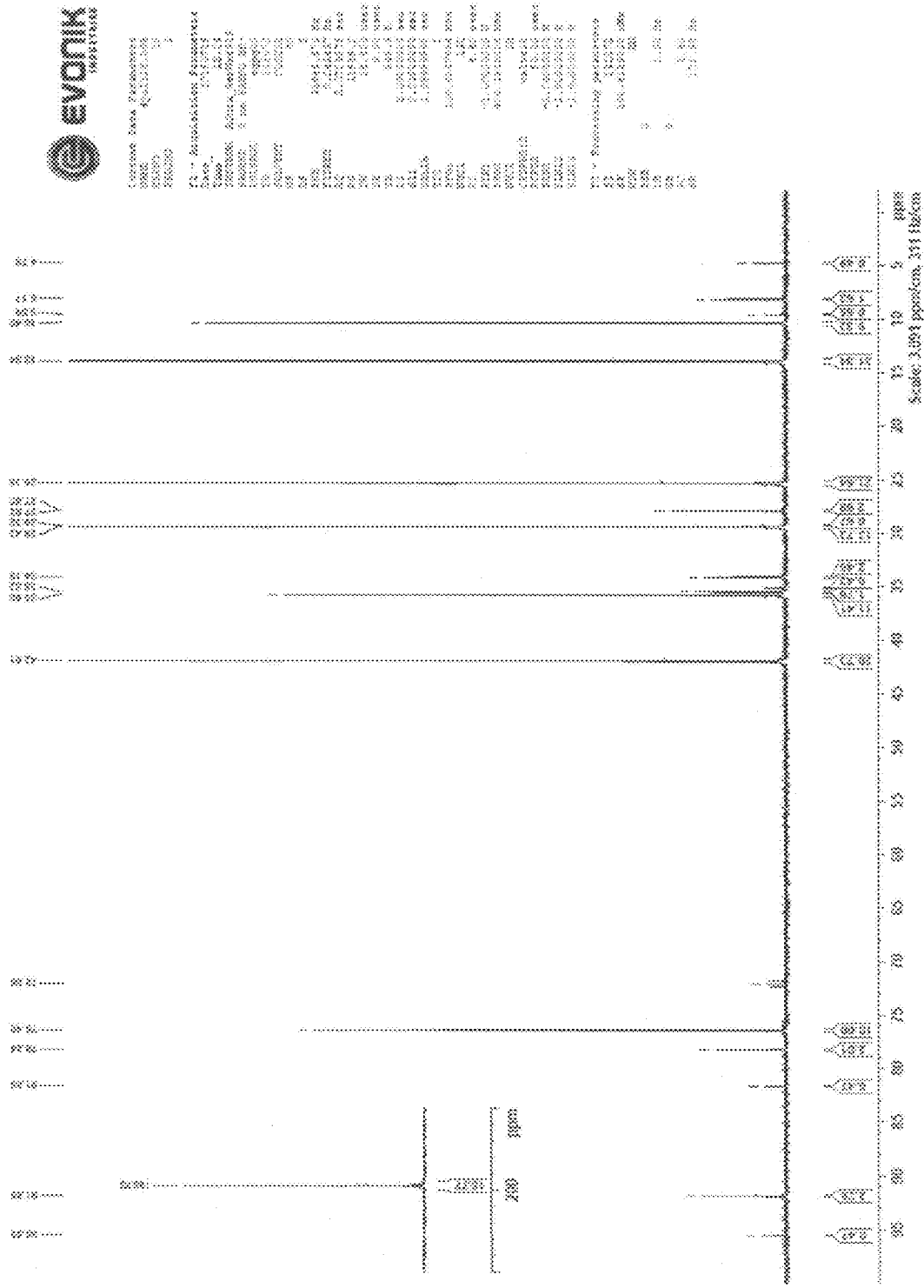
FIG. 1 Exemplary $^{13}$C-NMR spectrum (100 MHz, without solvent) of a composition according to the invention.
Figure 2:
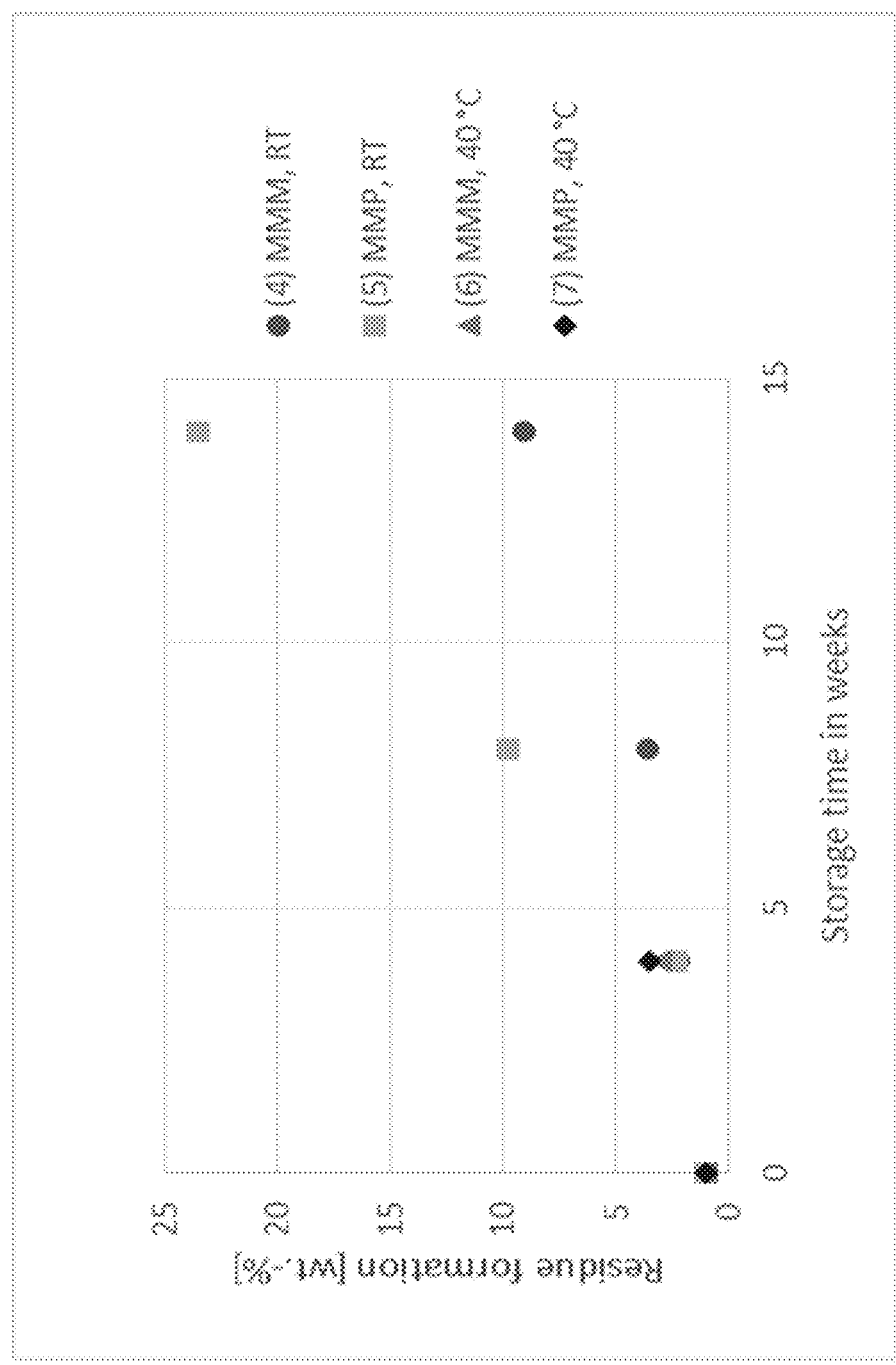
FIG. 2 Correlation of residue formation and time for examples 4 to 7 (first test series) (RT=room temperature; MMM=1-(1,3-bis(methylthio)propoxy)-3-(methylthio)propan-1-ol; MMP=3-methylthiopropionaldehyde).

The present invention therefore relates to a compound of the formula (I)

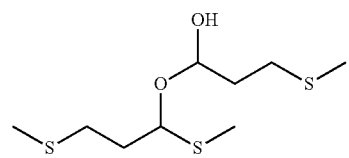

The name of this compound according to IUPAC (International Union of Pure and Applied Chemistry) nomenclature is 1-(1,3-bis(methylthio)propoxy)-3-(methylthio)propan-1-ol.

Due to the two stereocentres in this molecule, this compound is in the form of one or more of the stereoisomers 1-(1R,3-bis(methylthio)propoxy)-3-(methylthio)propan-1R-ol, 1-(1R,3-bis(methylthio)propoxy)-3-(methylthio)propan-1S-ol, 1-(1S,3- bis(methylthio) propoxy)-3-(methylthio)propan-1R-ol, 1-(1S,3-bis(methylthio)propoxy)-3-(methylthio)propan-1S-ol or in the form of a mixture of two or more of these stereoisomers.

In one embodiment, the compound according to the invention is therefore
1-(1R,3-bis(methylthio)propoxy)-3-(methylthio) propan-1R-ol,
1-(1R,3-bis(methylthio)propoxy)-3-(methylthio) propan-1S-ol, 1-(1S,3-bis(methylthio)propoxy)-3-(methylthio)propan-1R-ol, 1-(1S,3-bis(methylthio)propoxy)-3-(methylthio)propan-1S-ol or a mixture of two or more thereof.

If in the context of the present invention the compound 1-(1,3-bis(methylthio)propoxy)-3-(methylthio)propan-1-ol is mentioned without stating any stereoconfiguration, this statement includes both all individual stereoisomers of the compound according to the invention and a mixture of two or more of these stereoisomers.

Investigations have shown that a composition comprising 3-methylthiopropionaldehyde and methyl mercaptan, which additionally comprises also a compound of the formula (I) according to the invention, has a significantly reduced formation of high-boiling by-products than a corresponding composition without the compound according to the invention. The reduction of the formation of high-boiling by-products in a composition comprising the compound of the formula (I) compared to a composition without this compound is more pronounced the longer the compositions in question are stored.

Methyl mercaptan adds readily to the carbon atom of the aldehyde group of 3-methylthiopropionaldehyde to form its hemithioacetal 1,3-bis(methylthio)-1-propanol. By addition of the hydroxyl function of 1,3-bis(methylthio)-1-propanol to the carbon atom of the aldehyde function of a further molecule of 3-methylthiopropionaldehyde, the compound of the formula (I) is then formed. The four compounds methyl mercaptan, 3-methylthiopropionaldehyde, 1,3-bis(methylthio)-1-propanol and 1-(1,3-bis(methylthio)propoxy)-3-(methylthio)propan-1-ol are therefore in equilibrium with one another.

The present invention further relates therefore to a composition comprising the compound of the formula (I) according to the invention, 3-methylthiopropionaldehyde, 1,3-bis(methylthio)-1-propanol and/or methyl mercaptan.

The proportions of the components in the composition according to the invention depend both on the ratio of 3-methylthiopropionaldehyde and methyl mercaptan, which are reacted to give 1-(1,3-bis(methylthio)propoxy)-3-(methylthio)propan-1-ol, and on the temperature and water content.

At a ratio used of 3-methylthiopropionaldehyde and methyl mercaptan of 1.8:1 and at temperatures between 10 and 70° C. and a water content of 3% by weight, a composition according to the invention comprises 56 to 64% by weight 1,3-bis(methylthio)-1-propanol, 24 to 32% by weight 3-methylthiopropionaldehyde, 0 to 1% by weight methyl mercaptan and 9 to 15% by weight 1-(1,3-bis(methylthio)propoxy)-3-(methylthio)propan-1-ol.

At a ratio used of 3-methylthiopropionaldehyde and methyl mercaptan of 2.2:1 and at temperatures between 10 and 70° C. and a water content of 3% by weight, a composition according to the invention comprises 42 to 46% by weight 1,3-bis(methylthio)-1-propanol, 35 to 42% by weight 3-methylthiopropionaldehyde, 0 to 1% by weight methyl mercaptan and 13 to 22% by weight 1-(1,3-bis(methylthio)propoxy)-3-(methylthio)propan-1-ol.

At a ratio used of 3-methylthiopropionaldehyde and methyl mercaptan of 2.7:1 and at temperatures between 10 and 70° C. and a water content of 3% by weight, a composition according to the invention comprises 25 to 36% by weight 1,3-bis(methylthio)-1-propanol, 40 to 50% by weight 3-methylthiopropionaldehyde, 0 to 1% by weight methyl mercaptan and 15 to 34% by weight 1-(1,3-bis(methylthio)propoxy)-3-(methylthio)propan-1-ol.

At a ratio used of 3-methylthiopropionaldehyde and methyl mercaptan of 3.8:1 and at temperatures between 10 and 70° C. and a water content of 3% by weight, a composition according to the invention comprises 23 to 27% by weight 1,3-bis(methylthio)-1-propanol, 56 to 62% by weight 3-methylthiopropionaldehyde, 0 to 0.5% by weight methyl mercaptan and 12 to 21% by weight 1-(1,3-bis(methylthio)propoxy)-3-(methylthio)propan-1-ol.

In one embodiment, the composition according to the invention therefore comprises, at a water content of 3% by weight, 20 to 70% by weight 1,3-bis(methylthio)-1-propanol, 20 to 70% by weight 3-methylthiopropionaldehyde, 0 to 5% by weight methyl mercaptan and 1 to 40% by weight 1-(1,3-bis(methylthio)propoxy)-3-(methylthio)propan-1-ol.

In a composition according to the invention which has been stored at a temperature of 40° C. over a period of 4 weeks, a residue formation (fraction of high-boiling components in the product) of 1.98% by weight, based on the total mass of the composition, is observed. In comparison to this, in industrially prepared 3-methylthiopropionaldehyde under the same storage conditions, an elevated residue formation of 2.52% by weight, based on the total mass, is observed. The differences between a composition according to the invention and pure 3-methylthiopropionaldehyde in terms of residue formation are more pronounced after a longer storage period. For instance, in a composition according to the invention which is stored at a temperature of 25° C. (room temperature) over a period of 14 weeks, a residue formation of 5.48% by weight, based on the total mass of the composition, is observed. In comparison to this, the residue formation in industrially prepared 3-methylthiopropionaldehyde, which is stored under the same conditions, is significantly higher at 13.78% by weight, based on the total mass of the composition. Both the compound according to the invention and the composition according to the invention comprising the compound according to the invention are therefore suitable for storage of 3-methylthiopropionaldehyde and methyl mercaptan. It is assumed that this suitability is due to the reversible bonding of two molecules of 3-methylthiopropionaldehyde per molecule of the compound of the formula (I). This is because the reactive aldehyde groups of the 3-methylthiopropionaldehyde molecules are protected by this reversible incorporation and are therefore no longer available for side reactions which are responsible for the residue formation. As a result, a reduced formation of high-boiling secondary components of 3-methylthiopropionaldehyde is therefore observed in a composition comprising the compound of the formula (I). Due to the reduced risk potential of the compound according to the invention or a composition according to the invention and the reduced formation of high-boiling secondary components, the compound according to the invention or a composition according to the invention is also suitable for the transport of 3-methylthiopropionaldehyde and/or methyl mercaptan.

Another subject-matter of the present invention is therefore also the use of the compound according to the invention and/or a composition according to the invention comprising the compound according to the invention for the storage and/or transport of 3-methylthiopropionaldehyde and/or methyl mercaptan.

The storage or transport is preferably effected at a temperature of not more than 40° C., particularly preferably at a temperature of not more than 25° C., in particular, at a temperature of not more than 15° C. With regard to the time period of the storage or transport, the use according to the invention in principle has no limitations. The storage or transport may therefore occur over several weeks or even over several months. Over a period of 4, 8 or 14 weeks, a low formation of high-boiling by-products was observed for the compound according to the invention or a composition according to the invention. The storage is preferably effected at a temperature of not more than 40° C. for a time period of not more than 4 weeks. Alternatively, the storage is preferably effected at a temperature of not more than 25° C., in particular at a temperature of not more than 15° C., over a period of 4, 8 or up to 14 weeks.

In the simplest case, the compound according to the invention, independently of its individual stereoconfiguration, is obtained by reacting 3-methylthiopropionaldehyde with methyl mercaptan. In this reaction, the compounds 3-methylthiopropionaldehyde and methyl mercaptan, independently of each other either in pure form or in the form of streams or mixtures comprising 3-methylthiopropionaldehyde and methyl mercaptan, are brought into contact with each other. A mixture comprising 3-methylthiopropionaldehyde is preferably brought into contact with a mixture comprising methyl mercaptan, in order to obtain the compound according to the invention. This corresponds to the case, as can be found in an industrial configuration, where a mixture comprising 3-methylthiopropionaldehyde, a stream containing 3-methylthiopropionaldehyde for example, which originates from an upstream reaction, is brought into contact with a mixture comprising methyl mercaptan, a stream comprising methyl mercaptan from the production of methyl mercaptan for example, to obtain 1-(1,3-bis(methylthio)propoxy)-3-(methylthio)propan-1-ol. In this case, the streams in question comprising 3-methylthiopropionaldehyde and/or methyl mercaptan are not purified prior to the bringing into contact and the reaction to give the compound according to the invention. Alternatively, it is also possible to purify the streams in question prior to the bringing into contact and the reaction. In this case, a stream comprising purified or pure 3-methylthiopropionaldehyde, and/or a stream comprising purified or pure methyl mercaptan, is used in the reaction to give 1-(1,3-bis(methylthio)propoxy)-3-(methylthio)propan-1-ol. The stream or these streams may then contain the respective pure compounds undiluted as pure streams or diluted in an inert solvent.

The present invention therefore further provides a method for preparing a compound of the formula (I) comprising the step of
a) bringing a composition comprising or consisting of 3-methylthiopropionaldehyde into contact with a composition comprising or consisting of methyl mercaptan, to give a composition comprising the compound of the formula (I).

If the molar ratio of 3-methylthiopropionaldehyde to methyl mercaptan in this step is at least 2:1, the formation of the compound according to the invention is favoured.

Therefore, in one embodiment of the method according to the invention for preparing a compound of the formula (I), the molar ratio of 3-methylthiopropionaldehyde to methyl mercaptan in step a) is at least 2:1.

The molar ratio of 3-methylthiopropionaldehyde to methyl mercaptan in step a) of the method according to the invention is preferably between 2:1 and 4:1.

In order to achieve the highest possible yield of 1-(1,3-bis(methylthio)propoxy)-3-(methylthio)propan-1-ol, step a) of the method according to the invention for preparing a compound of the formula (I) is conducted at a temperature at which a comparatively large amount of methyl mercaptan is still present in the reaction mixture. This is because, with increasing temperature, the content of methyl mercaptan in a composition comprising 3-methylthiopropionaldehyde and methyl mercaptan decreases because of the high vapour pressure of methylmercaptan. The amount of methyl mercaptan present in reaction mixtures at a temperature of 70° C. is generally sufficient to produce 1-(1,3-bis(methylthio)propoxy)-3-(methylthio)propan-1-ol in large amounts.

In a further embodiment of the method according to the invention for preparing a compound of the formula (I), step a) is therefore conducted at a temperature of not more than 70° C.

Step a) of the method according to the invention for preparing a compound of the formula (I) is preferably conducted at a temperature of not more than 25° C.

Step a) of the method according to the invention for preparing a compound of the formula (I) is particularly preferably conducted under cooling, preferably at a temperature of not more than 15° C.

In this manner it is ensured that as little methyl mercaptan as possible escapes from the reaction solution and a correspondingly large amount of methyl mercaptan is incorporated into the compound 1-(1,3-bis(methylthio)propoxy)-3-(methylthio)propan-1-ol for storage.

The 3-methylthiopropionaldehyde used to prepare a compound of the formula (I) in step a) of the method according to the invention is preferably prepared by reacting acrolein with methyl mercaptan. In this reaction, the compounds acrolein and methyl mercaptan, independently of each other either in pure form or in the form of streams or mixtures comprising acrolein and methyl mercaptan, are brought into contact with each other. A mixture comprising acrolein is preferably brought into contact with a mixture comprising methyl mercaptan, in order to obtain 3-methylthiopropionaldehyde. This corresponds to the case, as can be found in an industrial configuration, where a mixture comprising acrolein, a stream containing acrolein for example, which originates from an upstream reaction, is brought into contact with a mixture comprising methyl mercaptan, a stream comprising methyl mercaptan from the production of methyl mercaptan for example, to obtain 3-methylthiopropionaldehyde. In this case, the streams in question comprising acrolein and/or methyl mercaptan are not purified prior to the bringing into contact and the reaction to give 3-methylthiopropionaldehyde. Alternatively, it is also possible to purify the streams in question prior to the bringing into contact and the reaction. In this case, a stream comprising purified or pure acrolein, and/or a stream comprising purified or pure methyl mercaptan, is used in the reaction to give 3-methylthiopropionaldehyde. The stream or these streams may then contain the respective pure compounds undiluted as pure streams or diluted in an inert solvent.

In one embodiment, the method according to the invention for preparing a compound of the formula (I) therefore additionally comprises the step upstream of step a) of
a') bringing a composition comprising or consisting of acrolein into contact with a composition comprising or consisting of methyl mercaptan, to give a composition comprising 3-methylthiopropionaldehyde.

Alternatively, it is also possible to react a portion of the compound of the formula (I) formed with acrolein to give 3-methylthiopropionaldehyde. In this manner, acrolein, which is associated with a high risk potential, is converted into the less hazardous compound 3-methylthiopropionaldehyde. By reacting the 3-methylthiopropionaldehyde thus obtained with methyl mercaptan, which is also said to have a high risk potential, the compound of the formula (I) is again formed. As a result, two substances with high risk potential are converted into the less hazardous compound of the formula (I).

In an alternative embodiment, the method according to the invention for preparing a compound of the formula (I) therefore additionally comprises the step upstream and/or downstream of step a) of a″) bringing a composition comprising the compound of the general formula (I) into contact with acrolein, to give a composition comprising 3-methylpropionaldehyde.

In the context of the method according to the invention for preparing a compound of the formula (I), it has proven to be advantageous if at least one of the steps a) or a') is carried out in the presence of a catalyst. In this case, a nitrogen-containing base has proven to be a suitable catalyst for both the reaction in step a) and for the reaction in step a'), wherein in one or both steps more than one nitrogen-containing base may also be present. Particularly in the formation of 3-methylthiopropionaldehyde from acrolein and methyl mercaptan, which proceeds as a 1,4-addition or Michael addition, a nitrogen-containing base has proven to be advantageous as catalyst.

In a further embodiment therefore, step a) and/or step a') of the method according to the invention for preparing a compound of the formula (I) are carried out in the presence of at least one nitrogen-containing base as catalyst. Preferably, at least step a') of the method according to the invention for preparing a compound of the formula (I) is carried out in the presence of a nitrogen-containing base as catalyst.

In a preferred embodiment of the method according to the invention for preparing a compound of the formula (I), the nitrogen-containing base is an unsubstituted or substituted N-heterocyclic compound or an amine of the formula $NR^1R^2R^3$, where $R^1$, $R^2$ and $R^3$ are either identical or different and are each independently of each other hydrogen, an alkyl residue having one to four carbon atoms or an arylalkyl residue having 7 to 14 carbon atoms, with the proviso that, if one of the residues $R^1$, $R^2$ or $R^3$ is hydrogen, the two other residues are not hydrogen.

If the nitrogen-containing base used in the method according to the invention is an N-heterocyclic compound, it is preferably pyridine or an alkyl-substituted pyridine such as picoline or lutidine. If the nitrogen-containing base used in the method according to the invention is an amine of the formula $NR^1R^2R^3$, it is preferably a tertiary amine, in particular a trimethylamine, triethylamine, tripropylamine, tributylamine, tridecylamine, tridodecylamine or dimethylbenzylamine, wherein dimethylbenzylamine is particularly preferred.

In the simplest case, the method according to the invention for preparing a compound of the formula (I) is carried out such that a composition comprising or consisting of 3-methylthiopropionaldehyde, which has been formed in a step upstream of step a), is added directly and without work-up to step a). Preferably, 3-methylthiopropionaldehyde is prepared by reacting acrolein or a mixture comprising acrolein or a stream comprising acrolein with methyl mercaptan or a mixture comprising methyl mercaptan or a stream comprising methyl mercaptan, which corresponds to step a') of a preferred embodiment of the method according to the invention for preparing a compound of the formula (I). Preferably, step a') of the method according to the invention is carried out in the presence of a nitrogen-containing base as catalyst. By supplying a composition comprising 3-methylthiopropionaldehyde obtained from step a') directly and without work-up to step a), the nitrogen-containing base is also supplied in this case to step a).

In another embodiment therefore, step a) and a') of the method according to the invention for preparing a compound of the formula (I) are carried out in the presence of at least one nitrogen-containing base as catalyst. Steps a) and a') are preferably carried out in the presence of the same base or the same bases.

Acrolein readily undergoes a radical or ionic polymerization, which can lead to significant losses of this economically relevant material of value. In the context of the method according to the invention it has been shown that by adjusting to a weakly acidic pH, the acrolein present in step a') of the method according to the invention can be stabilized, which is advantageous for a higher yield of 3-methylthiopropionaldehyde and thus also for a higher yield of 1-(1,3-bis(methylthio)propoxy)-3-(methylthio)propan-1-ol. The pH in step a') of the method according to the invention is preferably between 3 and 6. In the simplest case, the weakly acidic pH is set by the presence of one or more acids in step a'). Since step a') of the method according to the invention is carried out preferably in the presence of a nitrogen-containing base as catalyst, additional acid should be present in this step either in excess with respect to the base or the additional acid present should be correspondingly strong in order to set a (weakly) acidic pH in the presence of the base. If the composition comprising or consisting of 3-methylthiopropionaldehyde obtained in step a'), which has been prepared in the presence of an acid, is supplied without work-up to step a), then this step is also carried out in the presence of an acid.

In another embodiment therefore, step a) and/or step a') of the method according to the invention for preparing a compound of the formula (I) are carried out in the presence of at least one acid.

Step a) and/or step a') of the method according to the invention for preparing a compound of the formula (I) are carried out preferably in the presence of at least one nitrogen-containing base and at least one acid.

Both step a) and step a') of the method according to the invention for preparing a compound of the formula (I) are carried out preferably in the presence of at least one acid.

The acid is preferably a mineral acid, in particular hydrochloric acid, sulphuric acid or phosphoric acid, or an organic acid, in particular formic acid, acetic acid, propionic acid, lactic acid, succinic acid, tartaric acid, citric acid or a mixture of the acids stated above.

In the method according to the invention, metal cations, and particularly heavy metal cations such as $Fe^{2+}$, favour or even catalyze the formation of high boilers from aldehydes. By complexing metal cations, particularly heavy metal cations, the formation of undesirable high boilers is suppressed, which has a positive effect on the product purity and yield both in step a') and in step a) of the method according to the invention. With regard to the complexing agents suitable for complexing metal cations, the method according to the invention is in principle not subject to any limitations.

Suitable complexing agents in the context of the present invention are in principle all standard so-called polydentate complexing agents, that is all complexing agents having more than one functional group suitable for complex formation such as a hydroxyl, amino or carboxyl group. In the simplest case, the complexing agent is an organic acid having more than one carboxyl group, in particular tartaric acid.

Therefore, step a) and/or a') of the method according to the invention for preparing a compound of the formula (I) are preferably carried out in the presence of at least one complexing acid.

Since a nitrogen-containing base is also preferably present in step a) and/or a') of the method according to the invention for preparing a compound of the formula (I), step a) and/or a') of the method according to the invention for preparing a compound of the formula (I) is carried out in the presence of a nitrogen-containing base and a complexing acid. Preferably, the nitrogen-containing base is dimethylbenzylamine and the acid is acetic acid and/or tartaric acid. In particular, the nitrogen-containing base is dimethylbenzylamine and the acid is a mixture of acetic acid and tartaric acid.

The compound of the formula (I) according to the invention and the composition comprising this compound according to the invention may be reacted with acrolein to give 3-methylthiopropionaldehyde, which is an important material of value in the synthesis of the essential amino acid methionine. Moreover, by reacting acrolein with the compound according to the invention or the composition according to the invention comprising this compound, the compound acrolein that is linked to a high risk potential is converted into the compound 3-methylthiopropionaldehyde, which has a significantly lower risk potential.

The present invention therefore also relates to a method for preparing 3-methylthiopropionaldehyde comprising the step of bringing a composition comprising the compound of the formula (I) into contact with a composition comprising or consisting of acrolein, to obtain 3-methylthiopropionaldehyde.

The 3-methylthiopropionaldehyde obtained in this manner can be supplied to the generation of materials of value, such as the preparation of the essential amino acid methionine, or to the renewed preparation of the compound of the formula (I).

In accordance with the present invention, a compound of the formula (I) is prepared by bringing a composition or consisting of comprising 3-methylthiopropionaldehyde into contact with a stream comprising or consisting of methyl mercaptan, to give a composition comprising the compound of the formula (I). This corresponds to step a) of the method according to the invention for preparing a compound of the formula (I).

In one embodiment, the method according to the invention for preparing 3-methylthiopropionaldehyde therefore additionally comprises step a) of the method according to the invention for preparing a compound of the formula (I).

In accordance with the present invention, the 3-methylthiopropionaldehyde required for preparing a compound of the formula (I) is therefore prepared preferably by bringing a composition comprising or consisting of acrolein into contact with a composition comprising or consisting of methyl mercaptan to obtain a composition comprising 3-methylthiopropionaldehyde. This corresponds to step a') of the method according to the invention for preparing a compound of the formula (I). Alternatively, 3-methylthiopropionaldehyde can also be provided by step a'') of the method according to the invention for preparing a compound of the formula (I).

In a preferred embodiment, the method according to the invention for preparing 3-methylthiopropionaldehyde therefore additionally comprises step a') or a'') of the method according to the invention for preparing a compound of the formula (I).

EXAMPLES

Methods Used:
1. Residue Determination by Vacuum Distillation

The residue determination was carried out in a Kugelrohr evaporator of the GKR-50 type from Büchi. For this purpose, the empty weight of the reservoir used for the distillation was firstly determined. 15 g of the substance to be distilled were then weighed in and the reservoir introduced into the Kugelrohr evaporator. The heating of the distillation reservoir was set to 200° C., and a pressure of 30 mbar was set via the pressure regulator of the vacuum pump. The distillation was carried out on all samples over a period of 20 min. After cooling of the distillation apparatus, the apparatus was vented. The reservoir was then removed and weighed. The residue was determined using the following formula $$\text{Residue [wt.-\%]} = \frac{m \text{ (Residue)}}{m \text{ (Sample weight)}}$$

The residue determination has a precision of +/−0.1 wt.-%.

2. NMR Spectroscopic Investigations

The content of compounds present in equilibrium in a sample, methyl mercaptan, 3-methylthiopropionaldehyde, 1,3-bis(methylthio)-1-propanol and 1-(1,3-bis(methylthio)propoxy)-3-(methylthio)propan-1-ol, was determined by NMR spectroscopy (nuclear magnetic resonance) on a device of the type Advance 400 from Bruker.

For examples 1 to 3, $^{13}$C-NMR spectra of samples to which solvent had not been added were recorded at 100 MHz. From the recorded spectra, the molar ratios of the constituents to one another were read off. Tetrachloroethane-D2 was used as reference substance, which was introduced in a sealed capillary into the NMR tubes of the sample in question. For the ratio determination, characteristic signals of methyl mercaptan, 3-methylthiopropionaldehyde, 1,3-bis(methylthio)-1-propanol and 1-(1,3-bis(methylthio)propoxy)-3-(methylthio)propan-1-ol in the $^{13}$C-NMR spectrum were selected. These were, for methyl mercaptan the signal H$_3$CSH at 4.8 ppm, for 3-methylthiopropionaldehyde the signal —CH$_2$—CHO at 42.0 ppm, for 1,3-bis(methylthio)-1-propanol the signal —CH(OH)SCH$_3$ at 76.4 ppm and for 1-(1,3-bis(methylthio)propoxy)-3-(methylthio)propan-1-ol the signal H$_3$CS—CH$_2$—CH$_2$—CH(SCH$_3$)OR at 34.1 ppm, here the integral sum of both diastereomers was used.

For examples 4 to 8, $^1$H-NMR spectra of the samples in question were recorded at 400 MHz in deuterated dimethyl sulfoxide (d$_6$-DMSO). For the quantitative analysis, a known amount of naphthalene (10 mg of naphthalene at ca. 30 mg of sample in 0.7 mL of solvent) was added to the samples, and the content of methyl mercaptan, 3-methylthiopropionaldehyde, 1,3-bis(methylthio)-1-propanol and 1-(1,3-bis(methylthio)propoxy)-3-(methylthio)propan-1-ol was determined by means of the ratio of the characteristic signals to the integral for the napthalene internal standard.

FIG. 1 shows an exemplary $^{13}$C-NMR spectrum (100 MHz, without solvent, tetrachloroethane-D2 capillary) of a composition according to the invention (ratio of amounts of 3-methylthiopropionaldehyde to methyl mercaptan used for preparing compound (1) 2.7:1, mixture comprising 3% by weight water, measured without solvent at temperatures from 10 to 70° C. in steps of 10° C.), and Table 1 comprises an assignment of the characteristic $^{13}$C-NMR signals of the spectrum of the individual compounds.

TABLE 1

Assignment of the characteristic ¹³C-NMR signals of the individual compounds.

| Compound | δ/ppm | Assignment |
|---|---|---|
| A: 1,3-Bis(methylthio)-1-propanol | 10.4 | 4(A) |
| | 13.9 | 5(A) |
| | 29.4 | 3(A) |
| 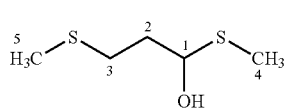 | 35.8 | 2(A) |
| | 76.4 | 1(A) |
| B: 3-Methylthiopropionaldehyde | 25.4 | 8(B) |
| | 42.0 | 7(B) |
| 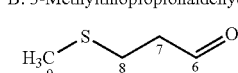 | 199.7 | 6(B) |
| C: Methyl mercaptan | 4.8 | 10(C) |
|  | | |
| D: 1-(1,3-Bis(methylthio)propoxy)-3-(methylthio)propan-1-ol | 8.2/9.6 | 16(D) |
| | 14.0 | 15/20(D) |
| | 27.9 | 19(D) |
| | 34.1 | 13(D) |
| 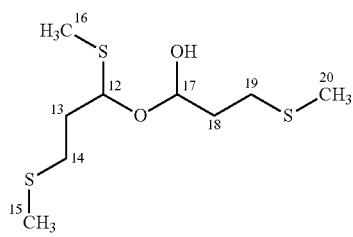 | 35.5/35.8 | 18(D) |
| | 78.2/81.7 | 12(D) |
| | 91.9/95.6 | 17(D) |
| Diastereomers | | |

3. Determination of Water Content by Karl Fischer Titration

The water content in compositions comprising 1-(1,3-bis(methylthio)propoxy)-3-(methylthio)propan-1-ol was determined according to the Karl Fischer method by titration using biamperometric indication of the end point. For this purpose, 20 to 30 ml of titration medium, e.g. Hydranal Solvent 5 from Fluka, were initially charged in the titration vessel and titrated to dryness with titrant, e.g. Hydranal Titrant 5 from Fluka. An amount of sample of ca. 500 mg was added to the dry-titrated reservoir using a plastic disposable syringe and titrated with the titrant to the end point. The precise sample weight was determined by differential weighing.

The performance of these standard methods is known to those skilled in the art and described extensively in the relevant literature, for example, in P. A. Bruttel, R. Schlink, "Wasserbestimmung durch Karl-Fischer-Titration" [Water Determination by Karl Fischer Titration], Metrohm AG, 2006.

4. Gas Chromatography

Gas chromatographic investigations were carried out using a gas chromatograph of the HP 6890 type from Agilent. The instrument was equipped with a capillary column of the DB-5 123-5033 type, 30 m×0.32 mm×1.0 μm, 5% phenylmethylpolysiloxane and a non-deactivated liner (ID 4 mm, Part No. 19251-60540). The analysis was conducted using a temperature gradient from 40 to 325° C. at a heating rate of 15° C. per minute.

In the context of the present invention, gas chromatography—in addition to other methods—was used for the determination of 3-methylthiopropionaldehyde, methyl mercaptan and acrolein.

Examples 1 to 3: Preparation of 1-(1,3-bis(methylthio)propoxy)-3-(methylthio)propan-1-ol Distilled 3-methylthiopropionaldehyde samples of industrial manufacture (97.1% by weight; 50.1 g (Example 1), 58.4 g (Example 2) and 40.1 g (Example 3)) were each initially charged in a flask, a catalyst mixture of N,N-dimethylbenzylamine (7.56% by weight, based on the catalyst mixture), acetic acid, tartaric acid and water was added, and the thus obtained mixtures were heated using a water bath. The amount of catalyst mixture added was selected so that the target concentration of N,N-dimethylbenzylamine in the 3-methylthiopropionaldehyde was 130 ppm. Methyl mercaptan (Sigma-Aldrich, 98.0% by weight; 10.7 g (Example 1), 10.0 g (Example 2) and 4.88 g (Example 3)) was initially charged in a cooled dropping funnel and added dropwise with stirring to the 3-methylthiopropionaldehyde so that a temperature of 15° C. was not substantially exceeded. The resulting product mixture was then stirred for 60 min at room temperature and analyzed by NMR spectroscopy. The maximum content of 1-(1,3-bis(methylthio)propoxy)-3-(methylthio)propan-1-ol was determined at 18.7 mol %, at a ratio of 3-methylthiopropionaldehyde to methyl mercaptan of 2.7:1. This corresponds to a content of 3% by weight water and a proportion by mass of around 32% by weight. The results of Examples 1 to 3 and the related investigations are summarized in Table 2.

TABLE 2

Overview of Examples 1 to 3 (MMP = 3-methylthiopropionaldehyde, MC = methyl mercaptan, MMP-MC = 1,3-bis(methylthio)-1-propanol, MMM = 1-(1,3-bis(methylthio)propoxy)-3-(methylthio)propan-1-ol)

| | Reactants | | Product composition | | | |
|---|---|---|---|---|---|---|
| | MMP | MC | MMP (mol %) | MC (mol %) | MMP-MC (mol %) | MMM (wt.-%)* |
| Example | (molar ratio) | | | | | |
| 1 | 2.2 | 1 | 49.9 | 0.0 | 39.2 | 11.0 | 20 |
| 2 | 2.7 | 1 | 56.8 | 0.0 | 24.6 | 18.7 | 32 |
| 3 | 3.8 | 1 | 70.4 | 0.0 | 20.4 | 9.2 | 18 |

*approximate values.

Examples 4 to 11: Storage Stability of Mixtures Comprising 1-(1,3-bis(methylthio)propoxy)-3-(methylthio)propan-1-ol 245.0 g of 3-methylthiopropionaldehyde of industrial manufacture (92.5% by weight) was initially charged in a flask and temperature-controlled with an ice-water bath. Methyl mercaptan (Sigma-Aldrich, 98.0% by weight, 36.21 g, 40.69 mL) was placed in a cooled dropping funnel, wherein the amount of methyl mercaptan relative to the initially charged 3-methylthiopropionaldehyde was selected such that a molar ratio of 3-methylthiopropionaldehyde to methyl mercaptan of approximately 3:1 resulted. The methyl mercaptan was added dropwise with stirring to the 3-methylthiopropionaldehyde so that a temperature of 15° C. was not substantially exceeded. After completion of the addition of the methyl mercaptan to the 3-methylthiopropionaldehyde, the resulting product mixture was stirred for a further 90 minutes at room temperature. A portion of the product was characterized by Karl Fischer titration, NMR spectroscopy and residue determination by vacuum distillation. A further portion of the product was stored for several weeks at room temperature or at 40° C., and the residue was determined at regular intervals. The results of two test series (the first test series comprises examples 4 to 7 and the second test series comprises examples 8 to 11) thus performed are compiled in the Tables 3a and 3b. These results clearly show that a mixture also comprising 1-(1,3-bis (methylthio)propoxy)-3-(methylthio)propan-1-ol in addition to 3-methylthiopropionaldehyde has a distinctly reduced residue formation compared to a corresponding mixture without 1-(1,3-bis(methylthio)propoxy)-3-(methylthio)propan-1-ol.

The generally rapid increase in residue formation in the examples 4 to 7 (first test series) can be explained with the high initial value of the residue in the used starting materials. The residue formation increases exponentially, which means that is an autocatalytic process.

TABLE 3a

Overview of Examples 4 to 7 (MMM = 1-(1,3-bis(methylthio)propoxy)-3-(methylthio)propan-1-ol, MMP = 3-methylthiopropionaldehyde)

| Example | Conditions | Time (weeks) | MMM content (wt.-%) | Residue (wt.-%) | Residue increase (wt.-%) |
|---|---|---|---|---|---|
| 4 | MMM, RT | 0 | 23.3 | 0.98 | |
| | | 4 | 24.7 | 2.18 | +1.20 |
| | | 8 | 21.7 | 3.60 | +2.62 |
| | | 14 | —* | 9.08 | +8.10 |
| 5 | MMP, RT | 0 | — | 0.98 | |
| | | 4 | — | 2.29 | +1.31 |
| | | 8 | — | 9.80 | +8.82 |
| | | 14 | — | 23.58 | +22.60 |
| 6 | MMM, 40° C. | 0 | 23.3 | 0.98 | |
| | | 4 | 23.7 | 2.96 | +1.98 |
| 7 | MMP, 40° C. | 0 | — | 0.98 | |
| | | 4 | — | 3.50 | +2.52 |

*not determined

TABLE 3b

Overview of Examples 8 to 11 (MMM = 1-(1,3-bis(methylthio)propoxy)-3-(methylthio)propan-1-ol, MMP = 3-methylthiopropionaldehyde)

| Example | Conditions | Time (weeks) | Residue (wt.-%) | Residue increase (wt.-%) |
|---|---|---|---|---|
| 8 | MMM, RT | 0 | 0.04 | |
| | | 2 | 0.01 | −0.03 |
| | | 4 | 0.23 | +0.19 |
| | | 6 | 0.51 | +0.47 |
| | | 8 | 0.39 | +0.34 |
| | | 12 | 0.44 | +0.40 |
| | | 14 | 0.18 | +0.14 |
| 9 | MMP, RT | 0 | 0.00 | |
| | | 2 | 0.14 | +0.14 |
| | | 4 | 0.02 | +0.02 |
| | | 6 | 0.04 | +0.04 |
| | | 8 | 0.62 | +0.62 |
| | | 12 | 4.72 | +4.72 |
| | | 14 | 8.64 | +8.64 |
| 10 | MMM, 40° C. | 0 | 0.04 | |
| | | 2 | 0.18 | +0.13 |
| | | 4 | 0.30 | +0.26 |
| | | 6 | 0.88 | +0.84 |
| | | 8 | 0.42 | +0.38 |
| | | 12 | 5.47 | +5.42 |
| | | 14 | 10.51 | +10.47 |
| 11 | MMP, 40° C. | 0 | 0.00 | |
| | | 2 | 0.36 | +0.36 |
| | | 4 | 1.17 | +1.17 |
| | | 6 | 3.50 | +3.50 |
| | | 8 | 7.09 | +7.09 |
| | | 12 | 12.96 | +12.96 |
| | | 14 | 13.24 | +13.25 |

Example 12: Preparation of 3-methylthiopropionaldehyde 60.4 g of 3-methylthiopropionaldehyde of industrial manufacture (93.9% by weight, "reactant MMP" in Table 4) was initially charged in a flask and temperature-controlled with an ice-water bath.

Methyl mercaptan (98.0% by weight, 9.83 g) was placed in a cooled dropping funnel, wherein the amount of methyl mercaptan relative to the initially charged 3-methylthiopropionaldehyde was selected such that a molar ratio of 3-methylthiopropionaldehyde to methyl mercaptan of approximately 3:1 resulted. The methyl mercaptan was added dropwise with stirring to the 3-methylthiopropionaldehyde so that a temperature of 15° C. was not substantially exceeded. After completion of the addition of the methyl mercaptan to the 3-methylthiopropionaldehyde, the resulting product mixture was stirred for a further 90 minutes at room temperature. Characterization by NMR spectroscopy gave a content of 31.7% by weight 1-(1,3-bis(methylthio) propoxy)-3-(methylthio)propan-1-ol, 26.5% by weight 1,3-bis(methylthio)-1-propanol and 33.3% by weight 3-methylthiopropionaldehyde. The product mixture was then reacted with acrolein to give 3-methylthiopropionaldehyde. For this purpose, 51.6 g of the product mixture and 8.2 g of acrolein were added dropwise from separate dropping funnels with stirring at 60° C. within 28 min to 97.9 g of 3-methylthiopropionaldehyde (6 equivalents, 93.9% by weight, residue 0.2% by weight), which functioned as solvent. After completion of the addition, both reactants were stirred at 60° C. for a further 60 min. The resulting product mixture ("product MMP" in Table 4) was cooled to room temperature and characterized by GC analysis and residue determination.

The analysis results are summarized in Table 4. The 3-methylthiopropionaldehyde obtained by reacting a mixture comprising 1-(1,3-bis(methylthio)propoxy)-3-(methylthio)propan-1-ol with acrolein was of high purity. 1-(1,3-Bis(methylthio)propoxy)-3-(methylthio)propan-1-ol prepared according to the invention is therefore suitable for storage both of 3-methylthiopropionaldehyde and methyl mercaptan.

TABLE 4

Example 12 (MMM = 1-(1,3-bis(methylthio)propoxy)-3-(methylthio)propan-1-ol, MMP = 3-methylthiopropionaldehyde, MC = methyl mercaptan, AC = acrolein)

| | GC analysis | | | Residue |
|---|---|---|---|---|
| | MC [wt.-%] | AC [wt.-%] | MMP [wt.-%] | [wt.-%] |
| Reactant MMP before MMM preparation | 0.90 | 0.12 | 93.94 | 0.20 |

TABLE 4-continued

Example 12 (MMM = 1-(1,3-bis(methylthio)propoxy)-3-
(methylthio)propan-1-ol, MMP = 3-methylthiopropionaldehyde,
MC = methyl mercaptan, AC = acrolein)

|  | GC analysis | | | Residue |
| --- | --- | --- | --- | --- |
|  | MC [wt.-%] | AC [wt.-%] | MMP [wt.-%] | [wt.-%] |
| Product MMP after reaction of MMM with AC | 0.94 | 0.17 | 94.68 | 0.20 |

The invention claimed is:

1. A method for preparing a compound of formula (I):

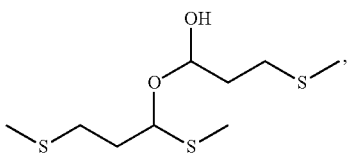

the method comprising:
a) bringing a composition comprising 3-methylthiopropionaldehyde into contact with a composition comprising methyl mercaptan, to obtain a composition comprising the compound of formula (I), wherein a molar ratio of 3-methylthiopropionaldehyde to methyl mercaptan in a) is between 2:1 and 4:1.

2. The method according to claim 1, wherein a) is conducted at a temperature of not more than 70° C.

3. The method according to claim 1, additionally comprising the step upstream of a) of
a') bringing a composition comprising acrolein into contact with a composition comprising methyl mercaptan, to obtain a composition comprising 3-methylthiopropionaldehyde.

4. The method according to claim 1, additionally comprising the step upstream and/or downstream of a) of
a") bringing a composition comprising the compound of formula (I) into contact with acrolein, to obtain a composition comprising 3-methylthiopropionaldehyde.

5. The method according to claim 3, wherein a) and/or a') are carried out in the presence of at least one nitrogen-containing base as catalyst.

6. The method according to claim 5, wherein the nitrogen-containing base is an unsubstituted or substituted N-heterocyclic compound or an amine of the formula $NR^1R^2R^3$, wherein $R^1$, $R^2$ and $R^3$ are either identical or different and are each independently of each other hydrogen, an alkyl residue having one to four carbon atoms or an arylalkyl residue having 7 to 14 carbon atoms, with the proviso that, if one of the residues $R^1$, $R^2$ or $R^3$ is hydrogen, the two other residues are not hydrogen.

7. The method according to claim 3, wherein step a) and/or step a') are carried out in the presence of at least one acid.

8. A method for preparing 3-methylthiopropionaldehyde, comprising bringing a composition comprising a compound of formula (I) obtained by the method accoring to claim 1, into contact with a composition comprising acrolein, to obtain a composition comprising 3-methylthiopropionaldehyde.

9. The method according to claim 8, additionally comprising:
a') bringing a composition comprising acrolein into contact with a composition comprising methyl mercaptan, to obtain a composition comprising 3-methylthiopropionaldehyde; or
a") bringing a composition comprising the compound of formula (I) into contact with acrolein, to obtain a composition comprising 3-methylthiopropionaldehyde.

10. The method according to claim 1, wherein a) is conducted at a temperature of not more than 25° C.

11. The method according to claim 1, wherein a) is conducted at a temperature of not more than 15° C.

12. The method according to claim 1, wherein the compound is at least one selected from the group consisting of:
1-(1R,3-bis(methylthio)propoxy)-3-(methylthio)propan-1R-ol,
1-(1R,3-bis(methylthio)propoxy)-3-(methylthio)propan-1S-ol,
1-(1S,3-bis(methylthio)propoxy)-3-(methylthio)propan-1R-ol, and
1-(1S,3-bis(methylthio)propoxy)-3-(methylthio)propan-1S-ol.

* * * * *